US012692474B2

(12) United States Patent
Sawyer et al.

(10) Patent No.: US 12,692,474 B2
(45) Date of Patent: Jul. 28, 2026

(54) MICROGEL PARTICLES FOR USE IN 3D PRINTING AND 3D CELL GROWTH MEDIUM AND RELATED COMPOSITIONS, SYSTEMS, AND METHODS

(71) Applicant: University of Florida Research Foundation, Inc., Gainesville, FL (US)

(72) Inventors: Wallace Gregory Sawyer, Gainesville, FL (US); Sangwoo Park, Gainesville, FL (US); Christopher S. O'Bryan, Philadelphia, PA (US); Christopher P. Kabb, Gainesville, FL (US); Brent S. Sumerlin, Gainesville, FL (US); Thomas Ettor Angelini, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1189 days.

(21) Appl. No.: 16/492,293

(22) PCT Filed: Mar. 9, 2018

(86) PCT No.: PCT/US2018/021804
§ 371 (c)(1),
(2) Date: Sep. 9, 2019

(87) PCT Pub. No.: WO2018/165584
PCT Pub. Date: Sep. 13, 2018

(65) Prior Publication Data
US 2020/0010798 A1 Jan. 9, 2020

Related U.S. Application Data

(60) Provisional application No. 62/616,107, filed on Jan. 11, 2018, provisional application No. 62/469,939, filed on Mar. 10, 2017.

(51) Int. Cl.
| | |
|---|---|
| *C12N 5/00* | (2006.01) |
| *B01J 13/00* | (2006.01) |
| *B33Y 70/00* | (2020.01) |
| *C08F 2/38* | (2006.01) |
| *C08F 220/26* | (2006.01) |
| *C08J 9/16* | (2006.01) |
| *C08L 33/26* | (2006.01) |
| *C12N 5/071* | (2010.01) |
| *C12P 21/00* | (2006.01) |

(52) U.S. Cl.
CPC ............ *C12N 5/0062* (2013.01); *B01J 13/00* (2013.01); *B33Y 70/00* (2014.12); *C08F 2/38* (2013.01); *C08F 220/26* (2013.01); *C08L 33/26* (2013.01); *C12P 21/00* (2013.01); *C08J 9/16* (2013.01); *C12N 5/0676* (2013.01)

(58) Field of Classification Search
CPC ........ C12N 5/0062; B01J 13/00; B33Y 70/00; C08F 2/38; C08F 220/26; C08F 220/56; C08F 220/06; C08L 33/26; C12P 21/00; C08J 9/16
See application file for complete search history.

(56) References Cited

U.S. PATENT DOCUMENTS

| | | | |
|---|---|---|---|
| 2,340,110 A | 1/1944 | D'Alelio | |
| 2,340,111 A | 1/1944 | D'Alelio et al. | |
| 2,533,635 A | 12/1950 | Seymour et al. | |
| 3,940,351 A | 2/1976 | Schlatzer, Jr. | |
| 4,062,817 A | 12/1977 | Westerman | |
| 5,034,486 A | 7/1991 | Tzai et al. | |
| 5,034,487 A | 7/1991 | Tzai et al. | |
| 5,034,488 A | 7/1991 | Tzai et al. | |
| 5,073,491 A | 12/1991 | Familletti | |
| 5,078,994 A | 1/1992 | Nair et al. | |

(Continued)

FOREIGN PATENT DOCUMENTS

| | | |
|---|---|---|
| GB | 2524232 A | 9/2015 |
| JP | 2005-027532 A | 2/2005 |

(Continued)

OTHER PUBLICATIONS

Saunders, Brian R., and Brian Vincent. "Microgel particles as model colloids: theory, properties and applications." Advances in colloid and interface science 80.1 (1999): 1-25. (Year: 1999).*
Kawaguchi, H. et al. Hydrogel Microspheres II. Precipitation Copolymerization of Acrylamide with Comonomers to Prepare Monodisperse Hydrogel Microspheres, 1991, Polymer Journal, 23(8): 955-962 (Year: 1991).*
Kobayashi, H. et al. Structure of Microgels with Debye-Huckel Interactions, 2014, Polymers, 6: 1602-16-17 (Year: 2014).*
Park, S. et al. Mechanical Properties of Surface-Charged Poly(Methyl Methacrylate) as Denture Resins, 2009, International Journal of Dentistry, v2009(841431): 1-6 (Year: 2009).*

(Continued)

*Primary Examiner* — Thomas J. Visone
(74) *Attorney, Agent, or Firm* — Thomas | Horstemeyer, LLP

(57) ABSTRACT

Microgel particles for use in a three-dimensional cell growth medium are described. The microgel particles may be swellable and may have properties conducive to improved function and health of cells distributed within the three-dimensional cell growth medium. Related compositions, systems, and methods are also described. Also provided is a plurality of microgel particles and a liquid cell culture medium, wherein the microgel particles are swelled with the liquid cell culture medium to form a granular gel. Also provided is a method of preparing a three-dimensional cell growth medium is disclosed. The method may comprise: mixing a plurality of microgel particles, such as those described above, in a liquid cell culture medium. Also provided is a method of placing cells in a three-dimensional cell growth medium is disclosed. Also provided is a method of synthesizing a protein is disclosed.

7 Claims, 13 Drawing Sheets

(56)                References Cited

U.S. PATENT DOCUMENTS

| 5,349,030 | A | 9/1994 | Long, II et al. |
| 7,049,346 | B1 | 5/2006 | Van Bladel et al. |
| 10,150,258 | B2 | 12/2018 | Feinberg et al. |
| 2006/0142404 | A1 | 6/2006 | Berge et al. |
| 2007/0111198 | A1 | 5/2007 | Santore et al. |
| 2007/0249044 | A1* | 10/2007 | Desai .................... C12M 25/14 |
| | | | 435/325 |
| 2010/0184147 | A1 | 7/2010 | Cheng et al. |
| 2014/0154737 | A1 | 6/2014 | Wellings |
| 2014/0295541 | A1 | 10/2014 | Nakanishi et al. |
| 2016/0167312 | A1 | 6/2016 | Feinberg et al. |

FOREIGN PATENT DOCUMENTS

| JP | 2011-072241 | A | 4/2011 | |
| JP | 2011-149024 | A | 8/2011 | |
| JP | 2017-012019 | A | 1/2017 | |
| JP | 2017-038568 | A | 2/2017 | |
| WO | WO-2010147632 | A1 * | 12/2010 | ........... A61K 9/1635 |
| WO | 2012155110 | A1 | 11/2012 | |
| WO | 2014049204 | A1 | 4/2014 | |
| WO | 2014205261 | A1 | 12/2014 | |
| WO | 2015017421 | A2 | 2/2015 | |
| WO | WO2016182969 | A1 | 11/2016 | |
| WO | 2018187595 | A1 | 10/2018 | |
| WO | 2018187780 | A1 | 10/2018 | |

OTHER PUBLICATIONS

Thorne, J. et al. Microgel applications and its commercial considerations, 2011, Colloid and Polymer Science, 289:625-646 (Year: 2011).*
Son, K.H. et al. Synthesis and Characterization of Poly(Ethylene Glycol) Based Thermo-Responsive Hydrogels for Cell Sheet Engineering, 2016, Materials, 9(854): 1-3 (Year: 2016).*
Shibayama, M. et al, Shrinking Kinetics of Poly(N-isopropylacrylamide) Gels T-Jumped across Their Volume Phase Transition Temperatures, 1999, Macromolecules,32 (22): 7461-7468 (Year: 1999).*
Melekaslan, D. et al. Swelling of strong polyelectrolyte hydrogels in polymer solutions: effect of ion pair formation on the polymer collapse, 2000, Polymer 41:5737-5747 (Year: 2000).*
International Research Report for application PCT/US2018/021804, mailed May 11, 2018.
International Search Report for PCT/US2016/031385 mailed Aug. 11, 2016.
Bhattacharjee et al., Liquid-like Solids Support Cells in 3D, ACS Biomaterials Science & Engineering, vol. 2, No. 10, p. 1787-1795, 2016.
Jin et al., Granular gel support-enabled extrusion of three-dimensional alginate and cellular structurs, Biofabrication, vol. 8, 2016.
Search Report issued by the European Patent Office for application EP16793291, dated Feb. 5, 2019.
Hinton, et al. "Three-dimensional printing of complex biological structures by freeform reversible embedding of suspended hydrogels," Sci. Adv. 1:e1500758.
Hinton, et al. "3D Printing PDMS Elastomer in Hydrophilic Support Bath via Freeform Reversible Embedding." ACS Biomater. Sci. Eng., May 4, 2016 (web).
Search Report issued by the European Patent Office for application 18764853.0, Mailed Dec. 21, 2020.
Kashiwabara et al., Preparation of monodisperse, reactive hydrogel microspheres and their amphoterization, Colloid. Polym. Sci. 273:339-345, 1995.
Kamijo et al., Preparation and Structural Characterization of Hydrogel Microspheres, Polymer Journal, vol. 28, No. 4, p. 309-316, 1996.
Office Action issued by the Japanese Patent Office for application 2019-548685, mailed Dec. 14, 2021.
Office Action based on European Application 18764853.0 mailed Mar. 31, 2026.

* cited by examiner low charge density microgels

N = neutral monomer

Q = charged monomer $l_N$ = length of neutral monomer $l_Q$ = length of charged monomer

* average distance between charges:

$$d = \frac{n l_N + m l_Q}{m}$$

* Bjerrum length :

$$l_B = \frac{1}{4\pi\varepsilon\varepsilon_0}\frac{Q^2}{k_B T}$$

<u>low charge density</u>:

FIG. 7 microgels with varying charge density prepared through precipitation reactions

MAA: anionic microgels qDMAEMA: cationic microgels

CBMA: zwitterionic microgels

MICROGEL PARTICLES FOR USE IN 3D PRINTING AND 3D CELL GROWTH MEDIUM AND RELATED COMPOSITIONS, SYSTEMS, AND METHODS

CROSS-REFERENCE TO RELATED APPLICATIONS

This application claims benefit of U.S. Provisional Application No. 62/469,939, filed Mar. 10, 2017, and Application Ser. No. 62/616,107, filed Jan. 11, 2018, which are hereby incorporated herein by reference in their entirety.

STATEMENT REGARDING FEDERALLY SPONSORED RESEARCH OR DEVELOPMENT

This invention was made with Government Support under Grant No. DMR1352043 awarded by the National Science Foundation. The Government has certain rights in the invention.

TECHNICAL FIELD

Disclosed embodiments are related to compounds, methods and systems related to three-dimensional cell culture.

BACKGROUND

Conventional cell culture techniques involve growing cells on a two-dimensional (2D) substrate, such as a microwell plate or a Petri dish. Such 2D cell cultures often include a growth medium disposed on the substrate to promote cell growth. However, the 2D environment of conventional cell cultures is often a poor substitute for the three-dimensional (3D) environment experienced by cells in vivo. For example, the behavior of a cell is often highly dependent on the microenvironment around the cell; in a 2D cell culture the microenvironment around the cell may be different than what a cell would experience in a 3D microenvironment.

Accordingly, improved compositions and methods for the 3D cell growth medium are needed.

SUMMARY

Microgel particles for use in a three-dimensional cell growth medium (and related methods, uses, and compositions) are described. In some embodiments, a composition for use in a three-dimensional cell growth medium comprises a plurality of microgel particles. The microgel particles may comprise a crosslinked polymeric network. The crosslinked polymeric network may, in turn, comprise low charge density polymer molecules and a crosslinker. The low charge density polymer molecules may comprise a plurality of charged groups, wherein an average spacing between the charged groups is greater than $\frac{1}{4}$, $\frac{1}{2}$, 1 times, 1.5 times, or 2 times the Bjerrum length for the charged groups.

In some embodiments a method of forming microgel particles is provided. The method may comprise forming a solution comprising: a crosslinker; a first monomer; a second monomer, wherein the second monomer is an acidic monomer, a basic monomer, a permanently cationic monomer, or a zwitterionic monomer; an initiator; and a solvent. The method may further comprise initiating the formation of polymers in the solution; and precipitating the polymers out of the solution, wherein the polymers form microgel particles.

In some embodiments, a three-dimensional cell growth medium is provided. The medium may comprise a plurality of microgel particles, such as those described above, and a liquid cell culture medium, wherein the microgel particles are swelled with the liquid cell culture medium to form a granular gel.

In some embodiments, a method of preparing a three-dimensional cell growth medium is disclosed. The method may comprise: mixing a plurality of microgel particles, such as those described above, in a liquid cell culture medium.

In some embodiments, a method of placing cells in a three-dimensional cell growth medium is disclosed. The method may comprise depositing cells in a granular gel comprising a plurality of microgel particles, such as those described above, swelled with a liquid cell culture medium.

In some embodiments, a method of synthesizing a protein is disclosed. The method may comprise culturing cells in a vessel containing granular gel comprising the plurality of microgel particles swelled with a liquid cell culture medium; and extracting from the vessel the protein synthesized by the cultured cells.

Other advantages and features of the present invention will become apparent from the following detailed description of various non-limiting embodiments of the invention when considered in conjunction with the accompanying figures. Unless otherwise noted, all references cited herein are incorporated by reference in their entirety. In cases where the present specification and a document incorporated by reference include conflicting and/or inconsistent disclosure, the present specification shall control.

The details of one or more embodiments of the invention are set forth in the accompanying drawings and the description below. Other features, objects, and advantages of the invention will be apparent from the description and drawings, and from the claims.

DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIGS. 1A-1C are schematic representations and formulas for low charge density particles.

FIG. 3 is a schematic representation of the synthesis of anionic acrylamide hydrogels through precipitation polymerization, according to one set of embodiments.

FIG. 4 is a schematic representation of the synthesis of pH-responsive anionic acrylamide hydrogels through precipitation polymerization, according to one set of embodiments.

FIG. 5 is a schematic representation of the synthesis of pH-responsive cationic acrylamide hydrogels through precipitation polymerization, according to one set of embodiments.

FIG. 6 is a schematic representation of the synthesis of permanently cationic acrylamide hydrogels through precipitation polymerization, according to one set of embodiments.

FIG. 7 is a schematic representation of the synthesis of zwitterionic acrylamide hydrogels through precipitation polymerization, according to one set of embodiments.

DETAILED DESCRIPTION

Disclosed herein are compositions and methods that increase functionality of cells cultured in a 3D cell growth medium. Creating a 3D cell growth medium using the materials described herein can enable faster cell growth, faster cell migration, and/or more robust expression of fluorescent materials and/or proteins by cells grown in the medium. For example, the 3D cell growth media described herein can be constructed to provide for improved function and health of cells distributed within the 3D cell growth medium.

For example, 3D cell growth medium have been proposed using commercially available carbomers swollen with liquid cell culture medium. However, commercially available carbomers, such as have been used to form a 3D cell growth medium, tend to sequester nutrients from the liquid cell culture medium. In accordance with some embodiments, the 3D cell growth medium is prepared using microgels particles prepared with polymers that have a reduced affinity for nutrients, such as minerals (e.g., calcium), from the liquid cell culture medium used to swell the microgel particles.

The use of microgel particles having a low charge density as disclosed herein may, in some embodiments, lead to a 3D cell growth medium that performs far better than 3D cell growth medium prepared with materials with high charge density. As used herein, the term "low charge density" refers to a characteristic of microgel particles in which the average spacing between charged groups on the polymer backbones is near to or greater than the Bjerrum length for the system at standard ambient temperature (25° C.). In some embodiments of low charge density microgel particles, the average spacing between charged groups of the microgel particles is greater than a quarter, half, or three-quarters of the Bjerrum length for the system. In some embodiments, the average spacing between charged groups of the microgel particles is greater than the Bjerrum length for the system. In some embodiments, the average spacing between charged groups of the microgel particles is greater than 1.5 times, 2.0 times, 2.5 times, or 3.0 times that of the Bjerrum length for the system.

The Bjerrum length characterizes the crossover length at which charged groups on a polymeric backbone begin to electrostatically interact. Turning to the Drawings, FIGS.

Figure 1A:
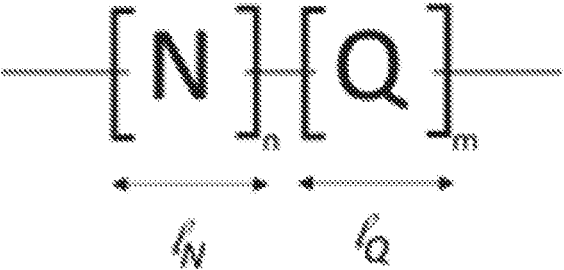
Figure 1B:
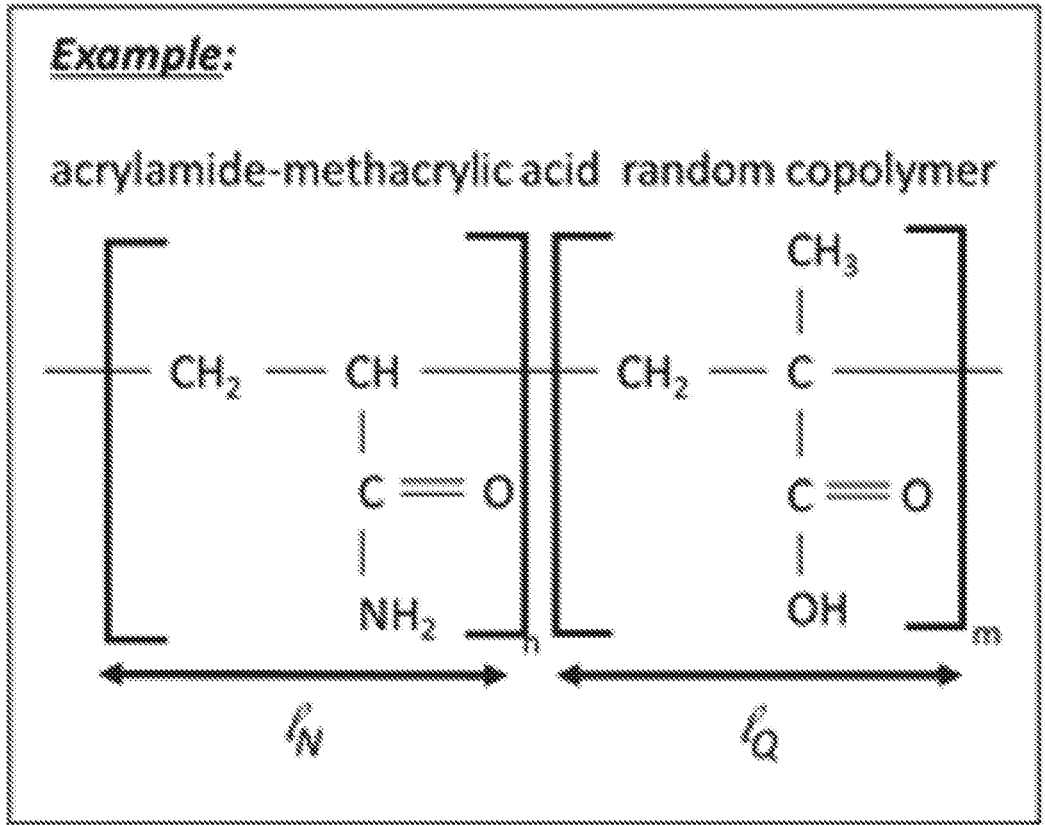

1A-1C help to further clarify the concepts of low charge density and Bjerrum length. FIG. 1A provides a schematic representation of a copolymer chain comprising neutral groups and charged groups. As one possible example of such a copolymer chain, FIG. 1B depicts a copolymer comprising neutral acrylamide groups or monomer units and charged methacrylic acid groups or monomer units. FIG. 1C provides formulas for determining the average distance between the charged groups of FIG. 1A, and for determining the Bjerrum length for the charged groups. As further indicated in FIG. 1C, a polymer having a low charge density is defined as one in which the average distance between charged groups is greater than the Bjerrum length for the system.

The average distance between charged groups is defined by Formula 1:

$$d = \frac{nl_N + ml_Q}{m} \tag{1}$$

in which d=the average distance between charges; n=the number of neutral monomers; m=the number of charged monomers; $l_N$=the length of neutral monomer; $l_Q$=the length of charged monomer.

The Bjerrum length for a system, such as a 3D cell growth medium, is defined by Formula 2:

$$l_B = \frac{1}{4\pi\varepsilon\varepsilon_0} * \frac{Q^2}{k_B T} \tag{2}$$

in which $l_a$=the Bjerrum length, $\varepsilon$=the dielectric constant of the medium (e.g., the 3D cell growth medium), $\varepsilon_0$=the vacuum permittivity constant, Q=the elementary charge, $k_B$=the Boltzmann constant; and T=the temperature of the system (e.g., the 3D cell growth medium).

Such polymers may be used to form microgel particles that may be swollen with a liquid cell culture medium. This results in a 3D cell growth medium that forms a "yield stress" material in which cells may be deposited, sometimes in predetermined patterns. The yield stress material can yield to enable growth of cell clusters.

According to some embodiments, when a 3D cell growth medium comprises low charge density microgel particles, the 3D cell growth medium will not sequester nutrients from the liquid cell culture medium. Such nutrients may, in some embodiments, be minerals. Such nutrients may, in some embodiments, be multivalent ions (e.g., calcium ions). However, when the average spacing between charged groups on the polymer backbone of the microgel particles is less or much less than the Bjerrum length (i.e., the particles have a high charge density), multivalent ions often will be sequestered. The sequestration of multivalent ions, such as calcium ions, may have significant negative impact on the function of and health of cells within the 3D cell growth medium. Therefore, the use of low charge density microgel particles disclosed herein may provide for improved function and health of cells within the 3D cell growth medium. The low charge density particles disclosed herein may provide desired swelling abilities, while avoiding the disadvantages related to the health and viability of cells caused by high charge density particles.

The 3D cell growth media described herein may allow for growing diverse cellular structures, including, but not limited to, spheroids, embryoid bodies, tumors, cysts, and microtissues, and may also be used to preserve the structure of cell-laden engineered tissue constructs. In some embodiments, a 3D cell growth medium may comprise a hydrogel comprising microgel particles dispersed in a liquid cell culture medium.

In accordance with some embodiments, the microgel particles may comprise a bio-compatible polymer and crosslinker. The polymer may serve as a polymer backbone to which the crosslinker bonds forming a polymeric network. The polymer may be a copolymer comprising a first and second monomer units. The first or primary monomer units may be neutral, while the second monomer units, or comonomer units may be charged. The components of the polymeric network may be chosen to facilitate the formation of low charge density microgel particles.

Monomers comprising the major percentage of the microgel particles may include acrylamides, N-alkylacrylamides, N,N-dialkylacrylamides, and acrylates. Non-limiting examples include acrylamide (AAm), N,N-dimethylacrylamide, N-isopropylacrylamide, poly(ethylene glycol) acrylate, poly(ethylene glycol) methacrylate, N-vinylcaprolactam, vinyl acetate, 2-hydroxyethyl acrylate, and N-vinylpyrrolidone.

The charged comonomers may comprise an ionizable (i.e., having acidic or basic functional groups) comonomer. In some cases, this comonomer may have an acidic functional group and be an acidic comonomer. Non-limiting examples of acidic comonomers include methacrylic acid, acrylic acid, sodium 4-styrene sulfonate, 2-acrylamido-2-methylpropane sulfonic acid, 2-carboxyethyl acrylate, and vinylbenzoic acid (all isomers). In some embodiments, the incorporation of acidic comonomer in the microgel particles is less than 20 mol %. In some embodiments, the incorporation of acidic comonomer may be about 0 mol % to about 30 mol %, about 0 mol % to about 20 mol %, about 0 mol % to about 15 mol %, about 0 mol % to about 10 mol %, or about 0 mol % to about 5 mol %.

The charged comonomers may comprise an ionizable (i.e., having acidic or basic functional groups) comonomer. In some cases, this comonomer may have a basic functional group and be a basic comonomer. Non-limiting examples of basic comonomers include 2-(dimethylamino)ethyl methacrylate, 2-(dimethylamino)ethyl methacrylate, 2-(dimethylamino)ethyl acrylate, 2-aminoethylmethacrylamide, aminopropyl)methacrylamide, and N-(3-dimethylaminopropyl) methacrylamide. In some embodiments, the incorporation of basic comonomer in the microgel particles is less than 30 mol %, such as less than 20 mol %. In some embodiments, the incorporation of acidic comonomer may be about 0 mol % to about 30 mol %, about 0 mol % to about 20 mol %, about 0 mol % to about 15 mol %, about 0 mol % to about 10 mol %, or about 0 mol % to about 5 mol %.

The charged comonomers may comprise a permanently ionized (i.e., having a permanent positive or negative charge, or both) comonomer. In some cases, this comonomer may have an permanently cationic functional group and be a permanently cationic comonomer. Non-limiting examples of permanently cationic comonomers include (3-acrylamidopropyl) trimethylammonium chloride, [2-(acryloyloxy) ethyl]trimethylammonium chloride, and (2-dimethylamino) ethyl methacrylate) methyl chloride. In some embodiments, the incorporation of acidic comonomer in the microgel particles is less than 20 mol %, In some embodiments, the incorporation of permanently cationic comonomer may be about 0 mol % to about 30 mol %, about 0 mol % to about 20 mol %, about 0 mol % to about 15 mol %, about 0 mol % to about 10 mol %, or about 0 mol % to about 5 mol %.

The charged comonomers may comprise a permanently ionized (i.e., having a permanent positive or negative charge, or both) comonomer. In some cases, this comonomer may have a zwitterionic (i.e., having both positive and negative charge) functional group and be a zwitterionic comonomer. Common zwitterionic groups include carboxybetaines, sulfobetaines, and phosphobetaines. Non-limiting examples of zwitterionic comonomers include 3-[[2-(methacryloyloxy)ethyl]dimethylammonio] propionate, [2-(methacryloyloxy)ethyl]dimethyl-(3-sulfopropyl)ammonium hydroxide, [3-(methacryloylamino)propyl]dimethyl(3-sulfopropyl)ammonium hydroxide, and (2-methacryloyloxyethyl phosphorylcholine). In some embodiments, the incorporation of zwitterionic comonomer in the microgel particles is less than 20 mol %. In some embodiments, the incorporation of acidic comonomer may be about 0 mol % to about 30 mol %, about 0 mol % to about 20 mol %, about 0 mol % to about 15 mol %, about 0 mol % to about 10 mol %, or about 0 mol % to about 5 mol %.

In some embodiments, the molar ratio of the first monomer and the second monomer may be controlled to provide the desired low charge density microgel particles. For example, in some embodiments, less than 60% of the sum of first and second monomers are second monomers (e.g., acidic, basic, permanently cationic, or zwitterionic comonomers). In some embodiments less than 50%, less than 40%, less than 30%, or less than 20% of the sum of first and second monomers are second monomers (e.g., acidic comonomers).

The crosslinker is typically a compound that can react with two or more polymer chains. In certain embodiments, for example, the crosslinker is a compound comprising at least two vinyl groups. In some cases, the crosslinker is a low-molecular-weight compound. Non-limiting examples of a suitable crosslinker include N,N-methylenebis(acrylamide) (MBA), diethylene glycol diacrylate, pentaerythritol triallyl ether, and N,N-ethylenebis(methacrylamide).

In some embodiments, the crosslinker is a polymer. In some embodiments the polymer may be a polyether. A non-limiting example of a suitable crosslinker is poly(ethylene glycol) diacrylate ("PEGda"). The crosslinker may be chosen having a suitable number average molecular weight to facilitate the formation of microgel particles with desired swelling properties. In some cases, the crosslinker has a number average molecular weight of between 250 g/mol and 10,000 g/mol. In some cases, the crosslinker has a number average molecular weight of at least about 500 g/mol, at least about 1000 g/mol, at least about 2000 g/mol, at least about 5000 g/mol, at least about 10,000 g/mol, at least about 20,000 g/mol, or at least about 50,000 g/mol. In some embodiments, the crosslinker has a number average molecular weight in the range of about 500 g/mol to about 1000 g/mol, about 500 g/mol to about 2000 g/mol, about 500 g/mol to about 5000 g/mol, about 500 g/mol to about 10,000 g/mol, about 500 g/mol to about 20,000 g/mol, about 500 g/mol to about 50,000 g/mol, about 1000 g/mol to about 5000 g/mol, about 1000 g/mol to about 10,000 g/mol, about 1000 g/mol to about 20,000 g/mol, about 1000 g/mol to about 50,000 g/mol, about 2000 g/mol to about 5000 g/mol, about 2000 g/mol to about 10,000 g/mol, about 2000 g/mol to about 20,000 g/mol, about 2000 g/ml to about 50,000 g/mol, about 5000 g/mol to about 10,000 g/mol, about 5000 g/mol to about 20,000 g/mol, about 5000 g/mol to about 50,000 g/mol, about 10,000 g/ml to about 20,000 g/mol, or about 10,000 g/mol to about 50,000 g/mol.

An initiator generally refers to a material that can produce radical species under certain conditions (e.g., exposure to light and/or heat, or redox conditions). Initiators may include thermal initiators, including azo and peroxide compounds. Examples include, but are not limited to, azobisisobutyronitrile, 1,1'-azobis(cyclohexane-1-carbonitrile), 2,2'-azobis(4-methoxy-2,4-dimethylvaleronitrile), 2,2'-azobis(2,4-dimethylvaleronitrile), dimethyl 2,2'-azobis(2-methylpropionate), 2,2'-azobis(2-methylbutyronitrile), 2,2'-azobis(N-butyl-2-methylpropionamide), 2,2'-azobis[2-(2-imidazolin-2-yl)propane]dihydrochloride, 2,2'-azobis(2-methylpropionamidine)dihydrochloride, 2,2'-azobis[N-(2-carboxyethyl)-2-methylpropionamidine]tetrahydrate, 2,2'-azobis[2-(2-imidazolin-2-yl)propane], 4,4'-azobis(4-cyanovaleric acid), 2,2'-azobis[2-methyl-N-(2-hydroxyethyl)propionamide], benzoyl peroxide, dicumyl peroxide, tert-butyl peroxide, tert-butyl peroxybenzoate, tert-butylperoxy 2-ethylhexyl carbonate, lauroyl peroxide, and 2-butanone peroxide. Initiators may also include photoinitiators. Examples include, but are not limited to 2,2-dimethoxy-2-phenylacetophenone, an Irgacure initiator (e.g., Ciba® IRGACURE® 2959), or 2-hydroxy-4'-(2-hydroxyethoxy)-2-methylpropiophenone.

Polymerization can be initiated with a redox initiator system, which generally involves ammonium persulfate (APS) or potassium persulfate (KPS) and a diamine compound as an adjunct catalyst. Examples of diamines include TEMED and dimethylaminopropionitrile (DMPN).

The monomer concentration in the reaction mixture (e.g., the solution from which the microgel particles precipitate) may affect the properties of the resultant microgel particles. Monomer concentrations that may be used include, but are not limited to, about 0.01 M to about 0.1 M, about 0.1 M to about 1 M, about 1 M to about 2 M, about 0.1 M to about 0.8 M, about 0.1 M to about 0.6 M, about 0.1 M to about 0.4 M, and about 0.1 M to about 0.2 M.

The crosslinking density of the microgel particles may be controlled by the ratio of monomer to crosslinker in the reaction mixture. Monomer to crosslinker molar ratios include, but are not limited to, about 10:1, about 20:1, about 50:1, about 100:1, about 150:1, or about 200:1. Ranges may also be formed from these ratios (e.g., from about 10:1 to about 20:1).

According to some embodiments, methods may be implemented to form microgel particles. The method may comprise, forming a solution comprising: a crosslinker; a first monomer; a second monomer, wherein the second monomer is an acidic monomer, a basic monomer, a permanently cationic monomer, or a zwitterionic monomers; an initiator; and a solvent. The method may further comprise initiating the formation of polymers in the solution; and precipitating the polymers out of the solution, wherein the polymers form microgel particles.

According to some embodiments, microgel particles are prepared using a precipitation polymerization method. In this technique, monomers are soluble in the reaction medium, however, the formed polymers are not. As polymers are formed, they become insoluble and precipitate from solution. In the case where a crosslinker is present, under certain conditions, discrete microgel particles may be formed.

A free-radical polymerization system generally comprises an initiator (e.g., a photoinitiator, a thermal initiator, a redox initiator) that can act as a radical source, one or more monomers (e.g., vinyl monomers), and, optionally, a solvent. The mechanism of a free radical polymerization is as follows. First, the initiator forms free radicals (e.g., through homolytic bond cleavage). In some cases, at least one of the free radicals may subsequently react with a monomer to form a monomer radical. The monomer radical may then react with one or more additional monomers to form an active polymer chain (i.e., a polymer radical). In some cases, active polymer chains may be terminated through bi-radical termination (e.g., combination or disproportionation) to form dead polymer chains that cannot react further (e.g., active polymer chain $P_n$ and active polymer chain $P_m$ react to form dead polymer chain or dead polymer chains $D_n$ and $D_m$).

In a precipitation polymerization, a solvent that solvates monomers and desolvates the formed polymers is necessary. Non-limiting examples of suitable solvents include ethanol, benzene, toluene, xylene, tetrahydrofuran (THF), 1,4-dioxane, anisole, N,N-dimethylformamide (DMF), N,N-dimethyl acetamide (DMAC), dimethyl sulfoxide (DMSO), water, methanol, hexane, heptane, and acetonitrile.

Polymerization temperatures may range from about 0° C. to about 120° C. In certain cases, the temperature at which polymerization is carried out is about 120° C. or less, about 110° C. or less, about 100° C. or less, about 90° C. or less, about 80° C. or less, about 70° C. or less, about 60° C. or less, about 50° C. or less, about 40° C. or less, about 30° C. or less, about 20° C. or less, about 10° C. or less, about 0° C. or less, or about −10° C. or less. In some embodiments, the temperature at which polymerization is carried out is in the range of about −10° C. to about 20° C., −10° C. to about 50° C., −10° C. to about 100° C., about 0° C. to about 20° C., about 0° C. to about 30° C., about 0° C. to about 40° C., about 0° C. to about 50° C., about 0° C. to about 100° C., about 10° C. to about 20° C., about 10° C. to about 30° C., about 10° C. to about 40° C., about 10° C. to about 50° C., about 10° C. to about 100° C., about 20° C. to about 30° C., about 20° C. to about 40° C., about 20° C. to about 50° C., about 20° C. to about 60° C., about 20° C. to about 70° C., about 20° C. to about 80° C., about 20° C. to about 90° C., about 20° C. to about 100° C., about 30° C. to about 50° C., about 30° C. to about 100° C., about 50° C. to about 60° C., about 50° C. to about 70° C., about 50° C. to about 80° C., about 50° C. to about 90° C., about 50° C. to about 100° C., about 50° C. to about 110° C., or about 50° C. to about 120° C.

The size of resulting individual microgel particles is measured using phase contrasted optical microscopy. The size of the microgel particles is preferred to be less than 10 µm. In some cases, the size of the microgel particles is less than 5 µm. In some cases, the size of the microgel particles is from 3 µm to 5 µm.

The resulting polymers may comprise crosslinked copolymers of monomer and ionizable comonomer. In certain embodiments, the resulting polymer has a number average molecular weight of at least about 500 g/mol, at least about 1000 g/mol, at least about 2000 g/mol, at least about 5000 g/mol, at least about 10,000 g/mol, at least about 20,000 g/mol, at least about 30,000 g/mol, at least about 40,000 g/mol, at least about 45,000 g/mol, at least about 50,000 g/mol, at least about 60,000 g/mol, at least about 70,000 g/mol, at least about 80,000 g/mol, at least about 90,000 g/mol, at least about 100,000 g/mol, at least about 200,000 g/mol, at least about 300,000 g/mol, at least about 400,000 g/mol, or at least about 500,000 g/mol. In some embodiments, the polymer comprising one or more dormant functional groups has a number average molecular weight in the range of about 500 g/mol to about 5000 g/mol, about 500 g/mol to about 10,000 g/mol, about 500 g/mol to about 20,000 g/mol, about 500 g/mol to about 30,000 g/mol, about 500 g/mol to about 40,000 g/mol, about 500 g/mol to about 45,000 g/mol, about 500 g/mol to about 50,000 g/mol, about 500 g/mol to about 60,000 g/mol, about 500 g/mol to about 70,000 g/mol, about 500 g/mol to about 80,000 g/mol, about 500 g/mol to about 90,000 g/mol, about 500 g/mol to about 100,000 g/mol, about 500 g/mol to about 200,000 g/mol, about 500 g/mol to about 300,000 g/mol, about 500 g/mol to about 400,000 g/mol, about 500 g/mol to about 500,000 g/mol, about 10,000 g/mol to about 20,000 g/mol, about 10,000 g/mol to about 30,000 g/mol, about 10,000 g/mol to about 40,000 g/mol, about 10,000 g/mol to about 45,000 g/mol, about 10,000 g/mol to about 50,000 g/mol, about 10,000 g/mol to about 60,000 g/mol, about 10,000 g/mol to about 70,000 g/mol, about 10,000 g/mol to about 80,000 g/mol, about 10,000 g/mol to about 90,000 g/mol, about 10,000 g/mol to about 100,000 g/mol, about 10,000 g/mol to about 200,000 g/mol, about 10,000 g/mol to about 300,000 g/mol, about 10,000 g/mol to about 400,000 g/mol, about 10,000 g/mol to about 500,000 g/mol, about 40,000 g/mol to about 50,000 g/mol, about 40,000 g/mol to about 60,000 g/mol, about 40,000 g/mol to about 70,000 g/mol, about 40,000 g/mol to about 80,000 g/mol, about 40,000 g/mol to about 90,000 g/mol, about 40,000 g/mol to about 100,000 g/mol, about 40,000 g/mol to about 200,000 g/mol, about 40,000 g/mol to about 300,000 g/mol, about 40,000 g/mol to about 400,000 g/mol, about 40,000 g/mol to about 500,000 g/mol, about 80,000 g/mol to about 100,000 g/mol, about 80,000 g/mol to about 200,000 g/mol, about 80,000 g/mol to about 300,000 g/mol, about 80,000 g/mol to about 400,000 g/mol, about 80,000 g/mol to about 500,000 g/mol, about 100,000 g/mol to about 200,000 g/mol, about 100,000 g/mol to about 300,000 g/mol, about 100,000 g/mol to about 400,000 g/mol, or about 100,000 g/mol to about 500,000 g/mol.

Number average molecular weight $M_n$ may be obtained by taking the number average of the molecular weights of individual polymer chains, according to Formula 3:

$$M_n = \frac{\sum M_i N_i}{\sum N_i} \tag{3}$$

where $N_i$ is the number of chains of molecular weight M. One method of measuring number average molecular weight is gel permeation chromatography.

According to some embodiments, a 3D cell growth medium may be prepared by dispersing microgel particles in a liquid cell culture medium. The microgel particles may be mixed with the liquid cell culture medium using a centrifugal mixer, a shaker, or any other suitable mixing device. During mixing, the microgel particles may swell with the liquid cell culture medium to form a material which is substantially solid when an applied shear stress is below a yield stress, as discussed above. After mixing, entrained air or gas bubbles introduced during the mixing process may be removed via centrifugation, agitation, or any other suitable method to remove bubbles from the 3D cell growth medium.

Hydrogels, such as a 3D cell growth medium, may be prepared by adding microgel particles to aqueous solutions at varying concentrations. In some embodiments the aqueous solution may comprise a liquid cell culture medium. As an example, polymer concentrations of less than 10 wt % (with respect to aqueous solution) may be used. Preferably, polymer concentrations of less than 5 wt % are used. Most preferably, polymer concentrations of less than 2 wt % are used.

In some embodiments, preparation of a 3D cell growth medium may also involve buffering to adjust the pH of a microgel particle and liquid cell culture medium mixture to a desired value. For example, some microgel particles may be made from polymers having a predominantly negative charge which may cause a 3D cell growth medium to be overly acidic (have a pH which is below a desired value). The pH of the 3D cell growth medium may be adjusted by adding a strong base to neutralize the acid and raise the pH to reach the desired value. Alternatively, a mixture may have a pH that is higher than a desired value; the pH of such a mixture may be lowered by adding a strong acid. According to some embodiments, the desired pH value may be in the range of between 5.5 and 6, or of between 4.5 and 8.

In one non-limiting example, a 3D cell growth medium comprises approximately 0.2% to about 0.7% by mass microgel particles. The microgel particles may be mixed with and swell with any suitable liquid cell growth medium, as described above, to form a 3D cell growth medium which comprises approximately 99.3% to about 99.8% by mass liquid cell culture medium.

When mixed with liquid cell culture medium, the microgel particles may swell with the liquid cell culture medium to form a granular hydrogel material that serves as a 3D cell growth medium. Depending on the particular embodiment, the swollen microgel particles may have a characteristic size at the micron or submicron scales. For example, in some embodiments, the swollen microgel particles may have a size between about 0.1 μm and 100 μm, between about 1 μm and 100 μm, between about 1 μm and 50 μm, or between about 0.1 μm and 50 μm. Other values are also possible.

As used herein, the term "microgel particle" refers to particles suitable for use in a hydrogel, and applies to the particle both when incorporated into a hydrogel and prior to or after incorporated into a hydrogel.

Any suitable liquid cell culture medium may be used. A particular liquid cell culture medium may be chosen depending on the types of cells which are to be placed within the 3D cell growth medium. Suitable liquid cell culture media may be human cell growth media, murine cell growth media, bovine cell growth media or any other suitable cell growth media. Depending on the particular embodiment, microgel particles and the liquid cell culture medium may be combined in any suitable combination. For example, in some embodiments, a 3D cell growth medium comprises approximately 0.5% to 1% microgel particles by weight.

Furthermore, a 3D cell growth medium may have any suitable combination of mechanical properties, and in some embodiments, the mechanical properties may be tuned via the relative concentration of microgel particles and the liquid cell culture medium. For example, a higher concentration of microgel particles may result in a 3D cell growth medium having a higher elastic modulus and/or a higher yield stress.

The disclosed tunability may be advantageous for controlling the environment around a group of cells placed in a 3D cell growth medium. For example, a 3D cell growth medium may have mechanical properties which are tuned to be similar to those found in vivo so that the cells 3D cell growth medium may emulate the natural environment of the cells. However it should be understood that the mechanical properties of a 3D cell growth medium may not be similar to those found in vivo, or may be tuned to any suitable values, as the disclosure is not so limited.

The elastic and shear moduli of the hydrogel is measured by performing an oscillatory frequency sweep at 1% strain across a wide range of frequencies. The elastic shear modulus of the hydrogel is preferred to dominate the viscous shear modulus with a relatively constant value of less than 100 Pa.

In some cases, the elastic shear modulus of the hydrogel is less than 50 Pa. In some cases, the elastic shear modulus of the hydrogel is about 10 Pa to about 100 Pa, about 10 Pa to about 80 Pa, about 10 Pa to about 60 Pa, about 10 Pa to about 40 Pa, or about 10 Pa to about 20 Pa.

The yield stress of the hydrogel system (e.g., 3D cell growth medium) corresponds to the shear rate independent stress value. The yield stress of the hydrogel is measured by applying a unidirectional shear rate to the hydrogel sample, recording the resulting shear stress and fitting a Hershel-Bulkley model to the resulting stress vs versus strain rate curve. The yield stress of the 3D cell growth medium can be less than 10 Pa. In some cases, the yield stress of the 3D cell growth medium is less than 5 Pa. In some cases, the yield stress of the 3D cell growth medium is about 5 Pa. In some cases, the yield stress of the 3D cell growth medium is about 1 Pa to about 10 Pa, about 1 Pa to about 8 Pa, about 1 Pa to about 6 Pa, about 1 Pa to about 4 Pa, or about 1 Pa to about 2 Pa.

According to some embodiments, a 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

The terms "yield stress" and "yield stress material" have been used and characterized in different ways in the art. For ease of description herein, the terms "yield stress" and "yield stress material" are used but, unless indicated otherwise, should be understood to be a Herschel-Bulkley yield stress determined using the Herschel-Bulkley equation $$\sigma = \sigma_y + k\gamma^{\&p}$$

where $\sigma_y$ is yield stress, $\sigma$ is shear stress, k is viscosity index of the material, $\gamma^{\&}$ is shear rate, and p is a positive number, and a material having such a yield stress.

In addition, "yield stress" (i.e., Herschel-Bulkley yield stress) has been measured in different ways in the art. Unless indicated otherwise herein, a yield stress of a sample is determined by shearing the sample in a rheometer using plate-plate geometry and via the Herschel-Bulkley equation, via the following process. Prior to shearing, the rheometer tool surfaces may be roughened to prevent or mitigate slipping at the sample-tool interface. Using the rheometer, the sample is sheared at a variety of shear rates, extending from high shear rates (e.g., 1000 s$^{-1}$) to low shear rates (0.001 s$^{-1}$). For each shear rate, the sample is sheared for 30 seconds, after which shear stress data is collected and averaged. A series of shear stress measurements are collected sequentially for each shear rate. These shear rates are then used, via the Herschel-Bulkley equation, to determine (1) whether the material has a yield stress (i.e., a Herschel-Bulkley yield stress), and (2) the yield stress for the material. Those skilled in the art will appreciate that, for a material having a yield stress, a plot of shear stress versus shear rate will exhibit a plateau region at low shear rates, with the data points asymptotically approaching the material's yield stress at low shear rates. The yield stress is the shear stress at these low, near-zero shear rates, or an estimate of shear stress at zero strain rate determined using a low or near-zero shear rate, such as a shear rate of 10$^{-3}$ s$^{-1}$. As used herein (unless indicated otherwise), a "yield stress material" will be a material that has a yield stress determinable via this process. Those skilled in the art will appreciate that for a yield stress material (i.e., a Herschel-Bulkley yield stress material) at low shear (e.g., a near-zero shear rate), a shear stress is independent of shear rate and instead exhibits only a shear stress dependent only on an elastic component of the material.

A 3D cell growth medium made from a yield stress material, as described above, may enable facile placement and/or retrieval of a group cells at any desired location within the 3D cell growth medium. For example, placement of cells may be achieved by causing a solid to liquid phase change at a desired location in a region of yield stress material such that the yield stress material will flow and be displaced when cells are injected or otherwise placed at the desired location. After injection, the yield stress material may solidify around the placed cells, and therefore trap the cells at the desired location.

However, it should be appreciated that any suitable techniques may be used to deposit cells or other biological materials within the 3D cell growth medium. For example, using a syringe, pipette or other suitable tool, cells may be injected into one or more locations in the 3-D growth medium. In some embodiments, the injected cells may be shaped as a pellet, such as by centrifugation. However, it should be appreciated that a 3D cell growth medium as described herein enables injection of cells suspended in a liquid, which may avoid a centrifugation step in conducting tests.

Regardless of how cells are placed in the medium, the yield stress of the yield stress material may be large enough to prevent yielding due to gravitational and/or diffusional forces exerted by the cells such that the position of the cells within the 3D cell growth medium may remain substantially constant over time. Since the cells are fixed in place, they may be retrieved from the same location at a later time for assaying or testing by causing a phase change in the yield stress material and removing the cells. As described in more detail below, placement and/or retrieval of groups of cells may be done manually or automatically.

A yield stress material as described herein may have any suitable mechanical properties. For example, in some embodiments, a yield stress material may have an elastic modulus between approximately 1 Pa and 1000 Pa when in a solid phase or other phase in which the material retains its shape under applied stresses at levels below the yield stress. In some embodiments, the yield stress required to transform a yield stress material to a fluid-like phase may be between approximately 1 Pa and 1000 Pa. When transformed to a fluid-like phase, a yield stress material may have a viscosity between approximately 1 Pa s and 10,000 Pa s. However, it should be understood that other values for the elastic modulus, yield stress, and/or viscosity of a yield stress material are also possible, as the present disclosure is not so limited.

In some embodiments, the yield stress may be tuned to match the compressive stress experienced by cell groups in vivo, as described above. Without wishing to be bound by any particular theory, a yield stress material which yields at a well-defined stress value may allow indefinite and/or unrestricted growth or expansion of a group of cells. Specifically, as the group of cells grows, it may exert a hydro-static pressure on the surrounding yield stress material; this hydrostatic stress may be sufficient to cause yielding of the yield stress material, thereby permitting expansion of the group of cells. In such embodiments, the yielding of the yield stress material during growth of a group of cells may result in the yield stress material maintaining a constant pressure on the group of cells during growth. Moreover, because a yield stress material will yield when an applied stress exceeds the yield stress, a 3D cell growth medium made from a yield stress material may not be able to apply a stress to a group of cells which exceeds the yield stress. The inventors have recognized and appreciated that such an upper bound on the stress applied to a group of cells may help to ensure that cells are not unnaturally constrained, damaged or otherwise altered due to the application of large compressive stresses.

According to some embodiments, a 3D cell growth medium made from a yield stress material may yield to accommodate excretions such as fluids or other extracellular materials from a group of cells disposed within the 3D cell growth medium. Without wishing to be bound by any particular theory, excretion of fluids or other materials from a group of cells may result in an increase in the pressure in the extracellular space; if the pressure exceeds the yield stress of the 3D cell growth medium, the 3D cell growth medium may yield to accommodate the excretions, and a group of cells may excrete fluids or other materials without restriction. Such an ability of a 3D cell growth medium to accommodate cellular excretion may allow the 3D cell growth medium to more closely match an in vivo environment. Moreover, the inventors have recognized and appreciated that a 3D cell growth medium made from a yield stress material may allow for facile removal of cellular excretions for assaying, testing, or any other suitable purpose, as described in more detail below.

A group of cells may be placed in a 3D cell growth medium made from a yield stress material via any suitable method. For example, in some embodiments, cells may be injected or otherwise placed at a particular location within the 3D cell growth medium with a syringe, pipette, or other suitable placement or injection device. In some embodiments an array of automated cell dispensers may be used to inject multiple cell samples into a container of 3-D growth medium. Movement of the tip of a placement device through the 3D cell growth medium may impart a sufficient amount of energy into a region around the tip to cause yielding such that the placement tool may be easily moved to any location within the 3D cell growth medium. In some instances, a pressure applied by a placement tool to deposit a group of cells within the 3D cell growth medium may also be sufficient to cause yielding such that the 3D cell growth medium flows to accommodate the group of cells. Movement of a placement tool may be performed manually (e.g. "by hand"), or may performed by a machine or any other suitable mechanism.

In some embodiments, multiple independent groups of cells may be placed within a single volume of a 3D cell growth medium. For example, a volume of 3D cell growth medium may be large enough to accommodate at least 2, at least 5, at least 10, at least 20, at least 50, at least 100, at least 1000, or any other suitable number of independent groups of cells. Alternatively, a volume of 3D cell growth medium may only have one group of cells. Furthermore, it should be understood that a group of cells may comprise any suitable number of cells, and that the cells may of one or more different types.

Depending on the particular embodiment, groups of cells may be placed within a 3D cell growth medium according to any suitable shape, geometry, and/or pattern. For example, independent groups of cells may be deposited as spheroids, and the spheroids may be arranged on a 3D grid, or any other suitable 3D pattern. The independent spheroids may all comprise approximately the same number of cells and be approximately the same size, or alternatively different spheroids may have different numbers of cells and different sizes. In some embodiments, cells may be arranged in shapes such as embryoid or organoid bodies, tubes, cylinders, toroids, hierarchically branched vessel networks, high aspect ratio objects, thin closed shells, or other complex shapes which may correspond to geometries of tissues, vessels or other biological structures.

According to some embodiments, a 3D cell growth medium made from a yield stress material may enable 3D printing of cells to form a desired pattern in three dimensions. For example, a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells. After injection, the 3D cell growth medium may transform back into a solid-like phase to support the printed cells and maintain the printed geometry. However, it should be understood that 3D printing techniques are not required to use a 3D cell growth medium as described herein.

A 3D cell growth medium made from a yield stress material may also allow for facile retrieval of groups of cells from within the cell growth medium via a reversal of the steps used to deposit the cells. For example, cells may be removed by simply moving a tip of a removal device such as a syringe or pipette to a location where a group of cells is disposed, and applying suction to draw the cells from the cell growth medium. As described above, movement of the tip of the removal device through the 3D cell growth medium may impart sufficient energy to the material to cause yielding and accommodate removal of the cells from the 3D cell growth medium. Such an approach may be used, for example, as part of a test process in which multiple cell samples are deposited in 3D cell growth medium. Those deposited cells may be cultured under the same conditions, but different ones of the samples may be exposed to different drugs or other treatment conditions. One or more samples may be harvested at different times to test impact of the treatment conditions on the cells.

In some embodiments, a 3D cell growth medium may be used to support and/or preserve the structure of a cell-laden engineered tissue construct. For example, a tissue construct including a scaffold or other suitable structure on which a plurality of cells is disposed may be placed into a 3D cell growth medium. The 3D cell growth medium may provide support to preserve a complex structure of the tissue construct while also providing a 3D environment for cell growth which may mimic that found in vivo.

It should be appreciated that one or more compounds may be deposited in conjunction with and/or adjacent to cells. For example, soluble, non-cellular components could be deposited in conjunction with the cells. These might include structural proteins (e.g. collagens, laminins), signaling molecules (growth factors, cytokines, chemokines, peptides), chemical compounds (pharmacologic agents), nucleic acids (e.g. DNA, RNAs), and others (nano-particles, viruses, vectors for gene transfer).

According to some embodiments, a method of synthesizing a protein is provided. Cells may be cultured in a vessel containing granular gel comprising the plurality of microgel particles swelled with a liquid cell culture medium. The protein synthesized by the cultured cells may then be extracted from the vessel. For example, in some embodiments, the cultured cells are pancreatic islet cells and the protein is insulin.

Figure 2A:
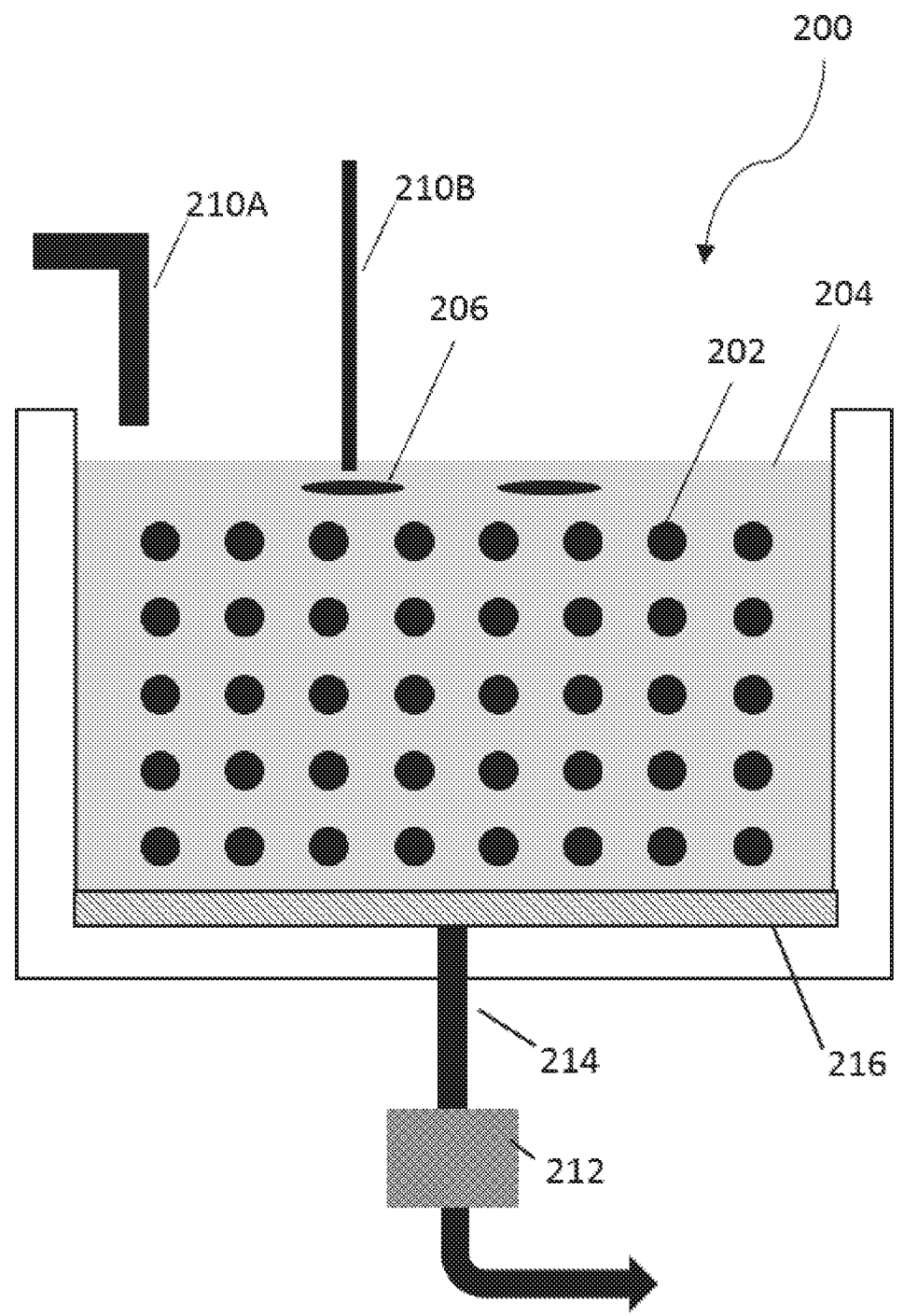
FIGS. 2A-2B illustrate examples of an apparatus for culturing and interacting with a 3D cell culture.
Figure 2B:
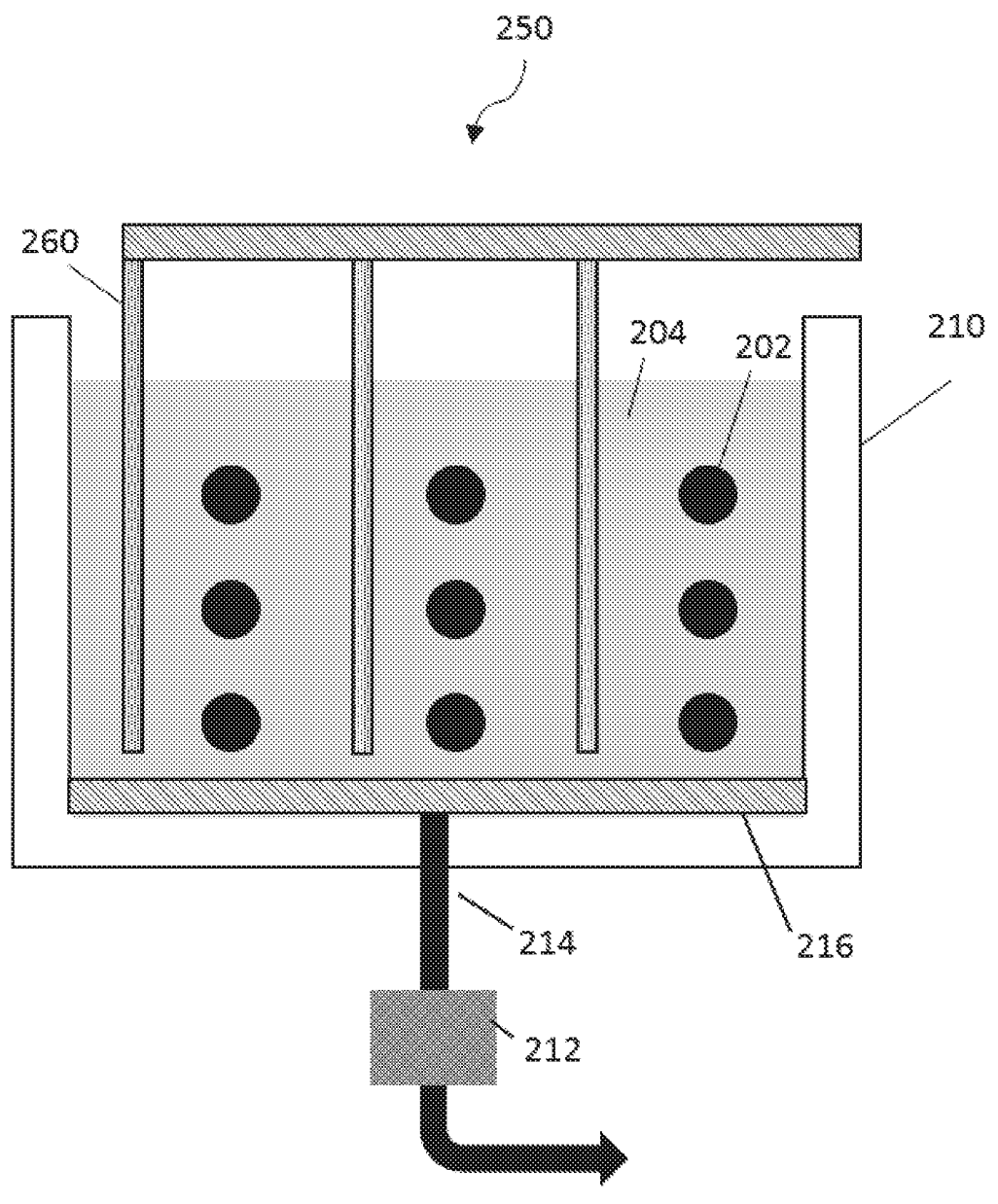

FIGS. 2A-2B illustrate examples of a cell culture and interaction apparatus, including examples of interaction equipment of such an apparatus.

FIG. 2A illustrates an apparatus 200 in which biological cells 202 are suspended at specific locations within a 3D cell growth medium 204. The apparatus includes interaction equipment 210A and 210B to dispense material into the 3D cell growth medium 204. Equipment 210A may dispense a liquid cell culture medium that, when combined with microgel particles, forms the 3D cell growth medium 204. The equipment 210A may dispense the liquid cell culture medium to supply nutrients as cells 202 absorb and use liquid cell culture medium from the 3D cell growth medium 204. Equipment 210B may also dispense material, such as by dispensing drug-loaded controlled release materials 206 into the 3D cell growth medium 204. The controlled release materials 206 may diffuse through the 3D cell growth medium 204 to be absorbed by the cells 202.

Apparatus 200 may further include interaction equipment to remove fluids from the 3D cell growth medium 204, As illustrated in FIG. 2A, the apparatus 200 may include a pump (e.g., a vacuum pump) 212, which may draw fluids out of the 3D cell growth medium 204 via an outflow 214. In some embodiments, as illustrated in FIG. 2A, the apparatus 200 may include a filter-like membrane 216, which may permit some materials to pass into the outflow 214 but may block a hydrogel of the 3D cell growth medium 204 or other materials from passing.

FIG. 2B illustrates another example of an apparatus 250, including different interaction equipment. Equipment and materials of the example of FIG. 2B that are the same as equipment/materials of FIG. 2A share the same reference numbers. The example of FIG. 2B illustrates perfusion tubing 260 to permit dispensing of one or more materials into the 3D cell growth medium 204. Three perfusion tubes are illustrated. The same materials may be dispensed from each tube 260, or different materials may be dispensed. The materials that may be dispensed include a liquid cell culture medium, pharmaceuticals, or other compounds.

The equipment 210E and 260 of the examples of FIGS. 3A and 3B may be operated, in some embodiments, to dispense materials at particular locations within the 3D cell growth medium 204 and, in some embodiments, may be operated to dispense materials to form a concentration gradient of the materials across the 3D cell growth medium 204. By forming a gradient, different cells 202 may be exposed to different concentrations of a material. Following exposure, the cells 202 may be inspected (within or outside of the 3D cell growth medium 204) to determine an impact of different concentrations of the materials on the cells 202.

In some embodiments, as discussed above, the equipment 210B and 260 of FIGS. 2A and 2B may be dynamically inserted and removed from the 3D cell growth medium 204, while the cells 202 are cultured in the 3D cell growth medium 204.

In the examples of FIGS. 2A and 2B, the pump 212 may be used to remove materials from the 3D cell growth medium 204 for any suitable purpose. For example, the pump 212 may be operated to remove a byproduct of cellular activity, including waste generated by the cells or a protein or other byproduct of cellular activity that is to be harvested. As another example, the pump 212 may impose a force on the 3D cell growth medium 204 so as to draw materials (e.g., materials dispensed by equipment 210A, 210B, 260) through the 3D cell growth medium 204. While a pump 212 is shown applying such a force in the examples of FIGS. 2A and 2B, in other embodiments the source of the force may be a centrifuge spinning the apparatus 200, 250, or gravity, or any other suitable source of a force.

These and other aspects of the present invention will be further appreciated upon consideration of the following Examples, which are intended to illustrate certain particular embodiments of the invention but are not intended to limit its scope, as defined by the claims.

EXAMPLES

The Examples below describe non-limiting embodiments of different aspects of the invention. Tables 1 and 2 provide summaries of key characteristics of the process parameters and hydrogels describes in the Examples below. Table 1 provides a summary of precipitation polymerization conditions. Table 2 provides a summary of properties of jammed hydrogels.

TABLE 1

| Example | Crosslinker | T (° C.) | EtOH (g) | [AAm]:[MAA]:[XL] |
|---|---|---|---|---|
| 1 | PEGda | 60 | 45 | 0.82:0.17:0.01 |
| 2 | PEGda | 60 | 95 | 0.82:0.17:0.01 |
| 3 | PEGda | 60 | 45 | 0.90:0.09:0.01 |
| 4 | PEGda | 60 | 45 | 0.83:0.17:0.002 |
| 5 | MBA | 60 | 45 | 0.90:0.09:0.01 |
| 6 | MBA | 60 | 45 | 0.81:0.17:0.02 |
| 7 | MBA | 60 | 45 | 0.82:0.17:0.01 |
| 8 | MBA | 60 | 95 | 0.82:0.17:0.01 |

TABLE 2

| Example | Polymer Concentration (wt %) | Elastic Shear Modulus (Pa) | Yield Stress (Pa) |
|---|---|---|---|
| 1 | 3 | 20 | 2 |
| 3 | 10 | 40 | 4 |
| 6 | 2 | 20 | 2 |

Example 1

This example describes a non-limiting process for forming microgel particles and the resultant particles. This example describes a composition comprising a monomer, an acidic comonomer, a crosslinker, a thermal initiator, and a solvent.

Figures 3, 4:
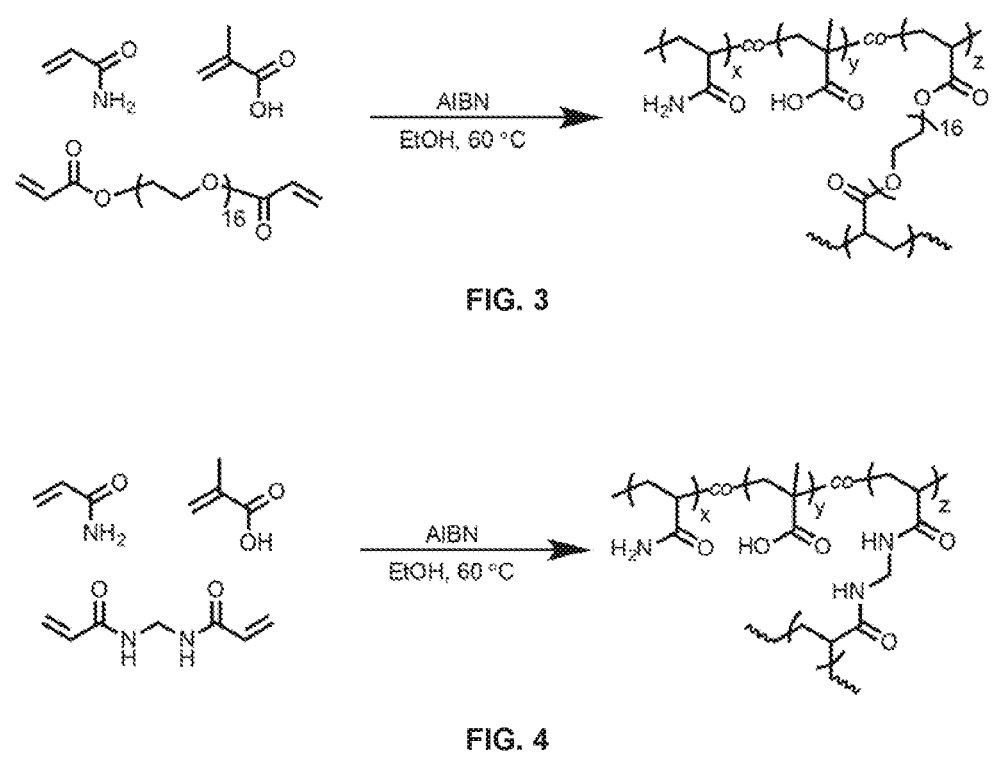

Acrylamide, methacrylic acid, and polyethylene glycol) diacrylate were dissolved in ethanol with a thermal initiator (AIBN) and heated. Ethanol, acrylamide, methacrylic acid, PEGda ($M_n$=700 g/mol), and AIBN were mixed in a 45:4:1:0.5:0.05 ratio (by weight). The mixture was purged with argon for 30 minutes to remove oxygen from the reaction. The flask was placed in a preheated oil bath at 60° C. for 4 h. As polymers were formed, they precipitated from solution as discrete microgel particles. FIG. 3 shows the reaction for the synthesis of anionic microgel particles. The molar ratio of monomers, as depicted in FIG. 3, are x=0.82, y=0.17, and z=0.01.

The microgel particles were filtered, resuspended in ethanol, filtered again, and dried overnight in a vacuum oven. The microgel particles had a diameter of approximately 1-3 μm. The elastic shear modulus of a hydrogel (3 wt % polymer) composed of these particles at 1 Hz was approximately 20 Pa. The yield stress of a hydrogel (3 wt % polymer) composed of these particles was approximately 2 Pa.

Example 2

This example describes a composition comprising a monomer, an acidic comonomer, a crosslinker, a thermal initiator, and a solvent. The molar ratio of monomers, as depicted in FIG. 3, were x=0.82, y=0.17, and z=0.01. Ethanol, acrylamide, methacrylic acid, PEGda ($M_n$=700 g/mol), and AIBN were mixed in a 95:4:1:0.5:0.05 ratio (by weight). The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven.

Example 3

This example describes a composition comprising a monomer, an acidic comonomer, a crosslinker, a thermal initiator, and a solvent. The molar ratio of monomers, as depicted in FIG. 3, were x=0.90, y=0.09, and z=0.01. Ethanol, acrylamide, methacrylic acid, PEGda ($M_n$=700 g/mol), and AIBN were mixed in a 45:4:0.5:0.5:0.05 ratio (by weight), The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven. The microgel particles had a diameter of 1-3 μm. The elastic shear modulus of a hydrogel (10 wt % polymer) composed of these particles at 1 Hz was approximately 40 Pa. The yield stress of a hydrogel (10 wt % polymer) composed of these particles was approximately 4 Pa.

Example 4

This example describes a composition comprising a monomer, an acidic comonomer, a crosslinker, a thermal initiator, and a solvent. The molar ratio of monomers, as depicted in FIG. 3, were x=0.83, y=0.17, and z=0.002. Ethanol, acrylamide, methacrylic acid, PEGda ($M_n$=700 g/mol), and AIBN were mixed in a 45:4:1:0.1:0.05 ratio (by weight). The mixture was purged with argon for 30 minutes to remove oxygen from the reaction. The flask was placed in a preheated oil bath at 60° C. for 4 h. The microgel particles are filtered, resuspended in ethanol, filtered again, and dried overnight in a vacuum oven.

Example 5

This example describes a composition comprising a monomer, an acidic comonomer, a crosslinker, a thermal initiator, and a solvent.

Acrylamide, methacrylic acid, and N,N-methylenebis(acrylamide) were dissolved in ethanol with a thermal initiator and heated. Ethanol, acrylamide, methacrylic acid, N,N-methylenebis(acrylamide), and AIBN were mixed in a 45:4:0.5:0.1:0.05 ratio (by weight). The mixture was purged with argon for 30 minutes to remove oxygen from the reaction. The flask was placed in a preheated oil bath at 60° C. for 4 h. FIG. 4 shows the synthesis reaction for the synthesized microgel particles. The molar ratio of monomers, as depicted in FIG. 4, were x=0.90, y=0.09, and z=0.01.

The microgel particles were filtered, resuspended in ethanol, filtered again, and dried overnight in a vacuum oven.

Example 6

This example describes a composition comprising a monomer, an acidic comonomer, a crosslinker, a thermal initiator, and a solvent. The molar ratio of monomers, as depicted in FIG. 4, were x=0.81, y=0.17, and z=0.02. Ethanol, acrylamide, methacrylic acid, N,N-methylenebis (acrylamide), and AIBN were mixed in a 45:4:1:0.2:0.05 ratio (by weight). The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven. The microgel particles had a diameter of approximately 2-4 μm. The elastic shear modulus of a hydrogel (2 wt % polymer) composed of these particles at 1 Hz was approximately 20 Pa. The yield stress of a hydrogel (2 wt % polymer) composed of these particles was approximately 2 Pa.

Example 7

This example describes a composition comprising a monomer, an acidic comonomer, a crosslinker, a thermal initiator, and a solvent. The molar ratio of monomers, as depicted in FIG. 4, were x=0.82, y=0.17, and z=0.01. Ethanol, acrylamide, methacrylic acid, N,N-methylenebis (acrylamide), and AIBN were mixed in a 45:4:1:0.1:0.05 ratio (by weight). The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven.

Example 8

This example describes a composition comprising a monomer, an acidic comonomer, a crosslinker, a thermal initiator, and a solvent. The molar ratio of monomers, as depicted in FIG. 4, were x=0.82, y=0.17, and z=0.01. Ethanol, acrylamide, methacrylic acid, N,N-methylenebis (acrylamide), and AIBN were mixed in a 95:4:1:0.1:0.05 ratio (by weight). The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven.

Example 9

Figures 5, 6:
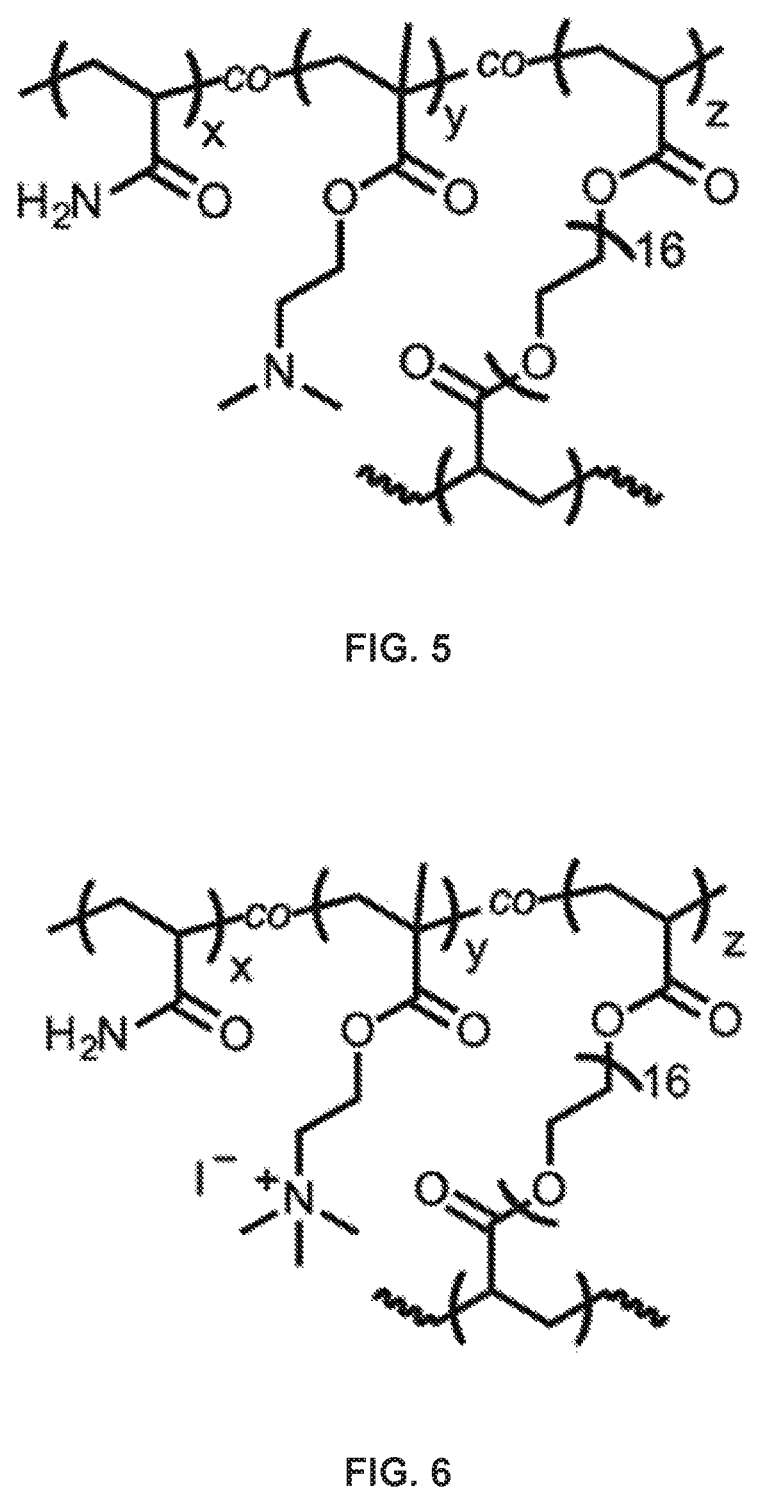

This example describes a composition comprising a monomer, a basic comonomer, a crosslinker, a thermal initiator, and a solvent. The molar ratio of monomers, as depicted in FIG. 5, were x=0.82, y=0.17, and z=0.01. Ethanol, acrylamide, 2-(dimethylaminoethyl)methacrylate, PEGda ($M_n$=700 g/mol), and AIBN were mixed. The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven.

Example 10

This example describes a composition comprising a monomer, a permanently cationic comonomer, a crosslinker, a thermal initiator, and a solvent. The molar ratio of monomers, as depicted in FIG. 6, were x=0.82, y=0.17, and z=0.01. Ethanol, acrylamide, [2-(acryloyloxy)ethyl]trimethylammonium iodide, PEGda (Mn=700 g/mol), and AIBN were mixed. The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven.

Example 11

Figure 7:
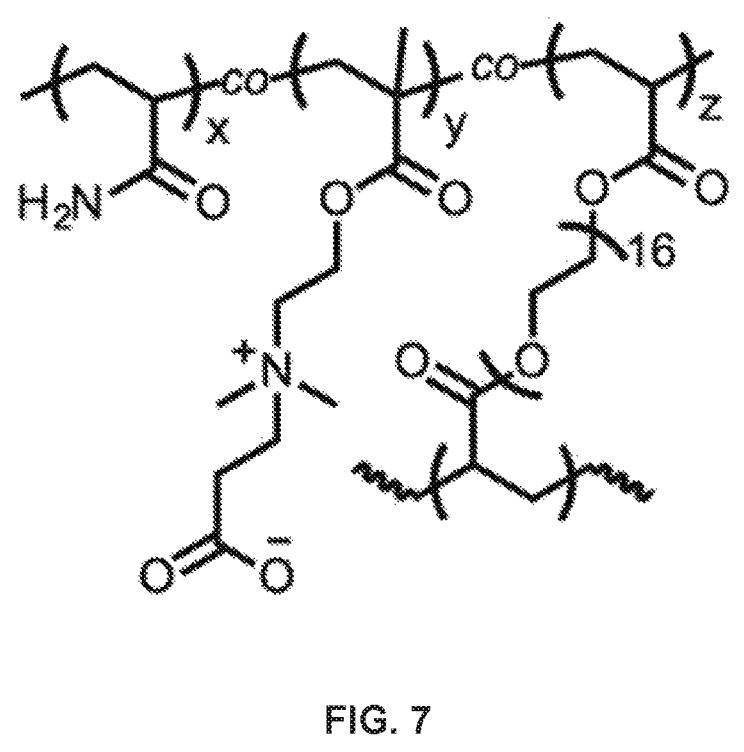

This example describes a composition comprising a monomer, a zwitterionic comonomer, a crosslinker, a thermal initiator, and a solvent. The molar ratio of monomers, as depicted in FIG. 7, were x=0.82, y=0.17, and z=0.01. Ethanol, acrylamide, 3-[[2-(methacryloyloxy)ethyl]dimethylammonio]propionate, PEGda (Mn=700 g/mol), and AIBN were mixed. The mixture was purged with argon for 30 minutes to remove oxygen from the reaction. The flask was placed in a preheated oil bath at 60° C. for 4 h. The microgel particles were filtered, resuspended in ethanol, filtered again, and dried overnight in a vacuum oven.

Example 13

Figure 8:
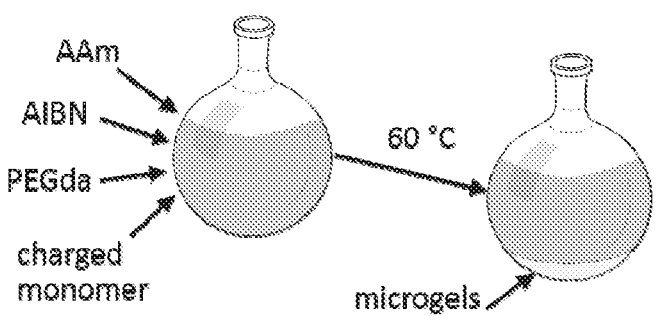
FIG. 8 illustrates a process for preparing polyelectrolyte microgels with varying charge density through precipitation reactions. MAA—methacrylic acid; CBMA—carboxy-betaine methacrylate; qDMAEMA—quadranized dimethyl-aminoehtyl methacrylate.
Figure 9A:
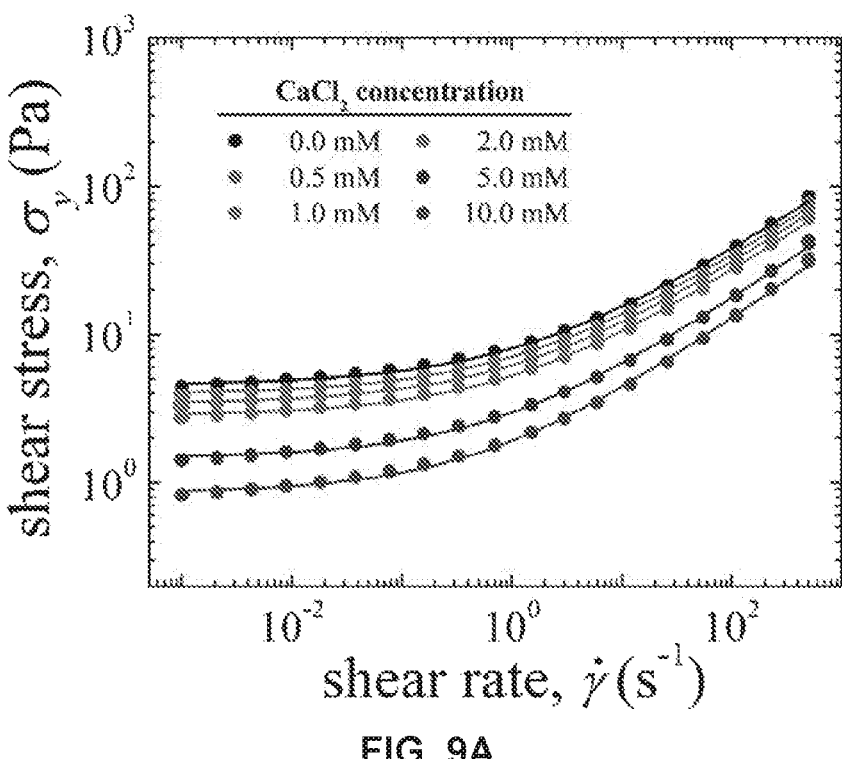
FIGS. 9A to 9D are graphs showing rheological changes in cationic microgels with added calcium.
Figure 9B:
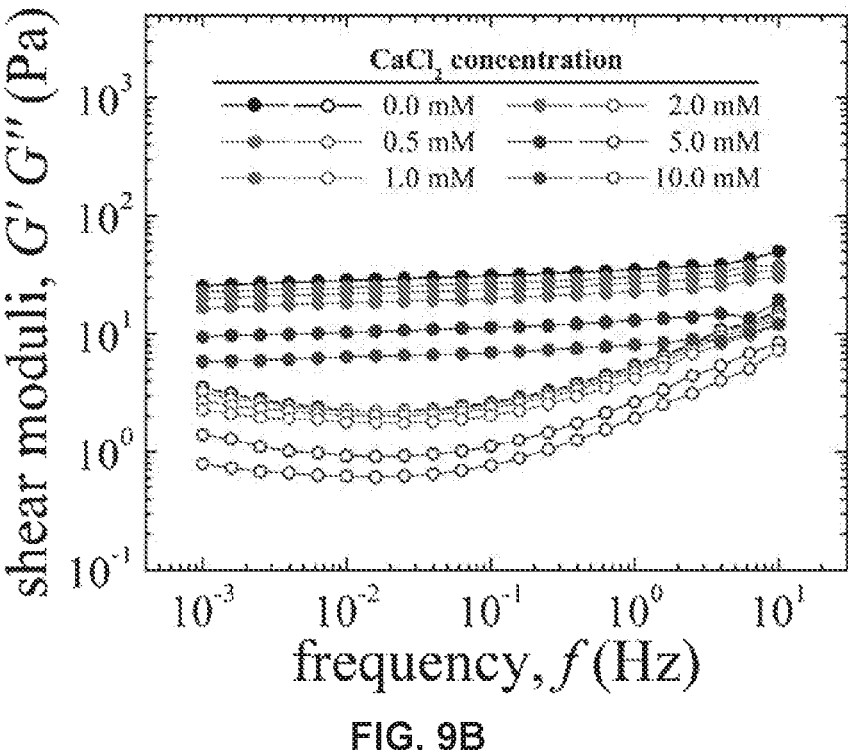
Figure 9C:
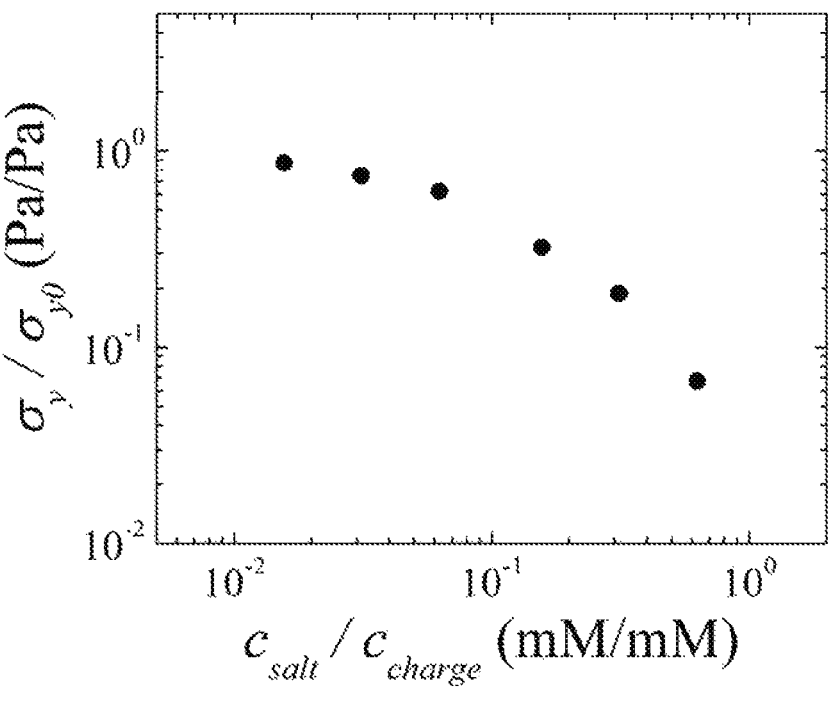
Figure 9D:
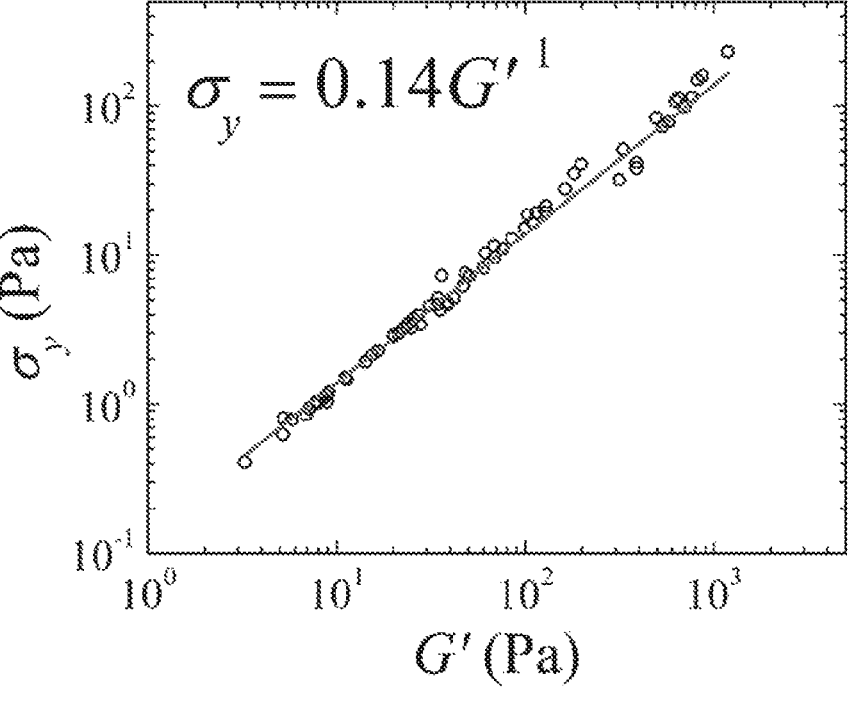

FIG. 8 illustrates a process for preparing polyelectrolyte microgels with varying charge density through precipitation reactions. MAA—methacrylic acid; CBMA—carboxybetaine methacrylate; qDMAEMA—quadranized dimethylaminoehtyl methacrylate.

FIGS. 9A to 9D are graphs showing rheological changes in cationic microgels with added calcium.

Figure 10:
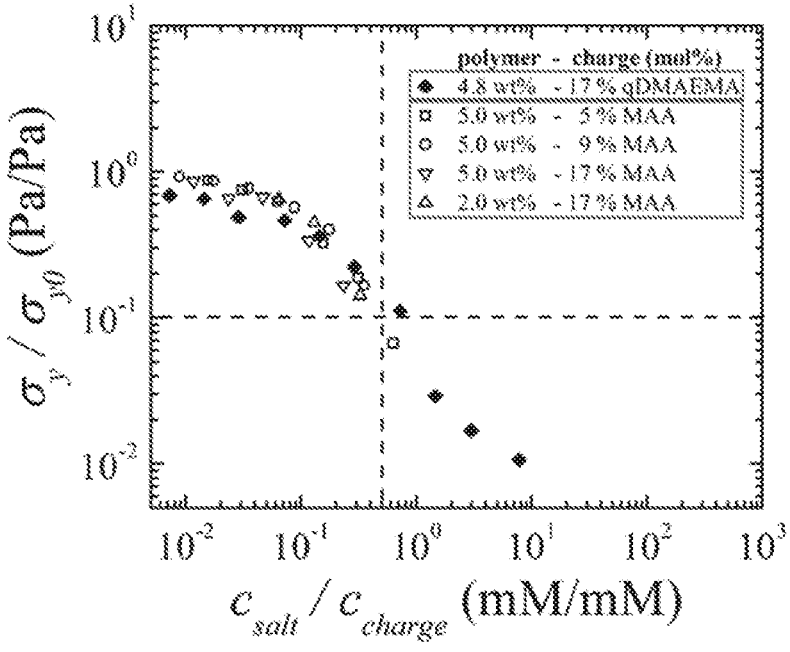
FIG. 10 is a graph showing yield stress ($\sigma_y/\sigma_{y0}$) as a function of $c_{salt}/c_{charge}$ (mM/mM) in anionic and cationic microgels.

FIG. 10 is a graph showing yield stress ($\sigma_y/\sigma_{y0}$) as a function of $c_{salt}/c_{charge}$ (mM/mM) in anionic and cationic microgels.

Figure 11:
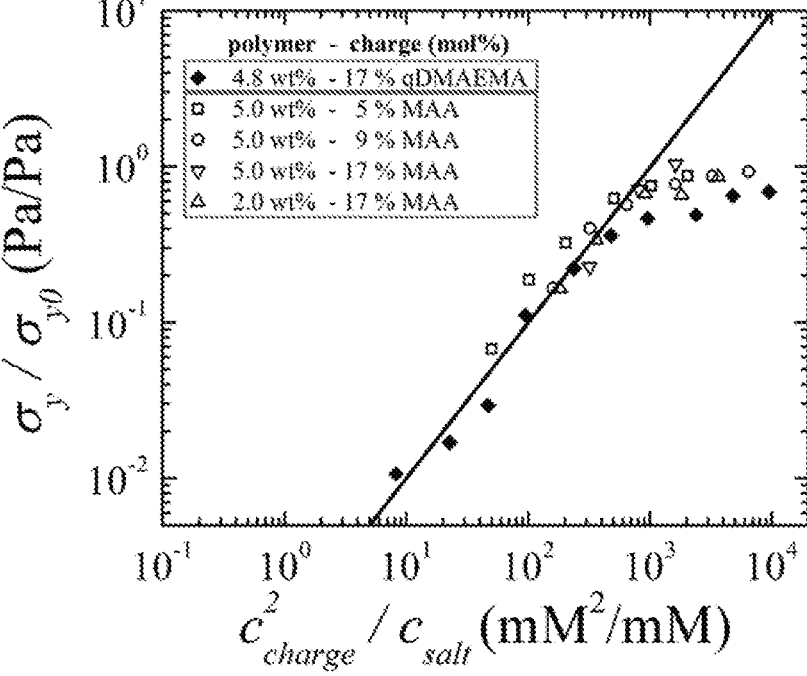
FIG. 11 is a graph showing yield stress ($\sigma_y/\sigma_{y0}$) as a function of $c^2_{charge}/c_{salt}$ (mM²/mM) in anionic and cationic microgels.

FIG. 11 is a graph showing yield stress ($\sigma_y/\sigma_{y0}$) as a function of $c^2_{charge}/c_{salt}$ (mM²/mM) in anionic and cationic microgels.

Figure 12:
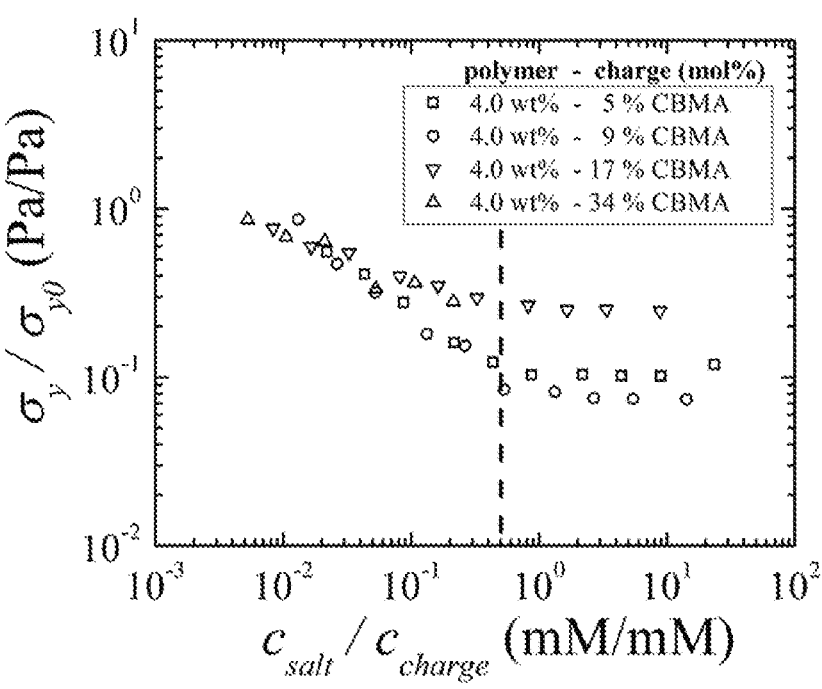
FIG. 12 is a graph showing yield stress ($\sigma_y/\sigma_{y0}$) as a function of $c_{salt}/c_{charge}$ (mM/mM) in zwitterionic microgels.

FIG. 12 is a graph showing yield stress ($\sigma_y/\sigma_{y0}$) as a function of $c_{salt}/c_{charge}$ (mM/mM) in zwitterionic microgels.

Figure 13:
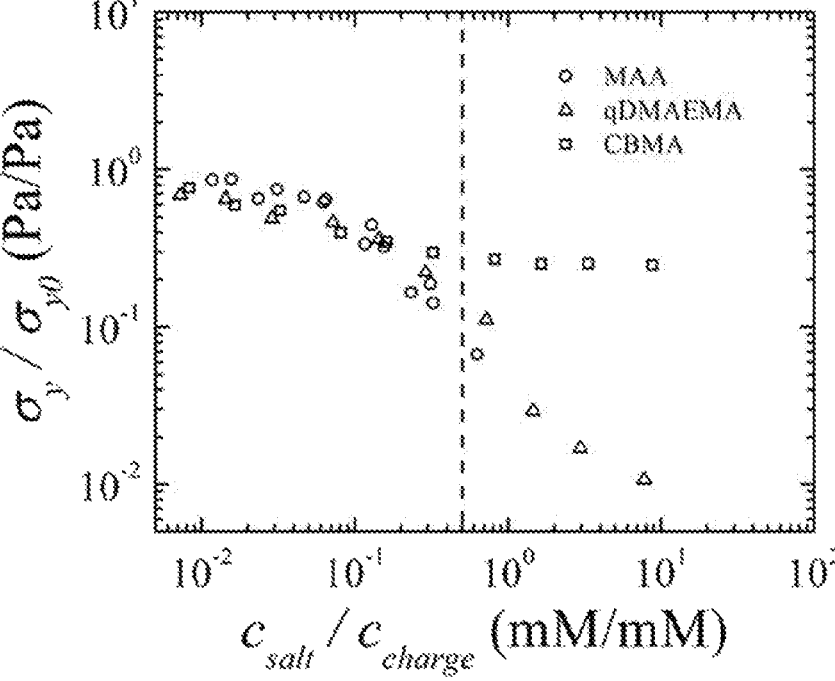
FIG. 13 is a graph showing yield stress ($\sigma_y/\sigma_{y0}$) as a function of $c_{salt}/c_{charge}$ (mM/mM) in anionic (MAA), zwitterionic (CBMA), and cationic (qDMAEMA) microgels.

FIG. 13 is a graph showing yield stress ($\sigma_y/\sigma_{y0}$) as a function of $c_{salt}/c_{charge}$ (mM/mM) in anionic (MAA), zwitterionic (CBMA), and cationic (qDMAEMA) microgels.

Figure 14:
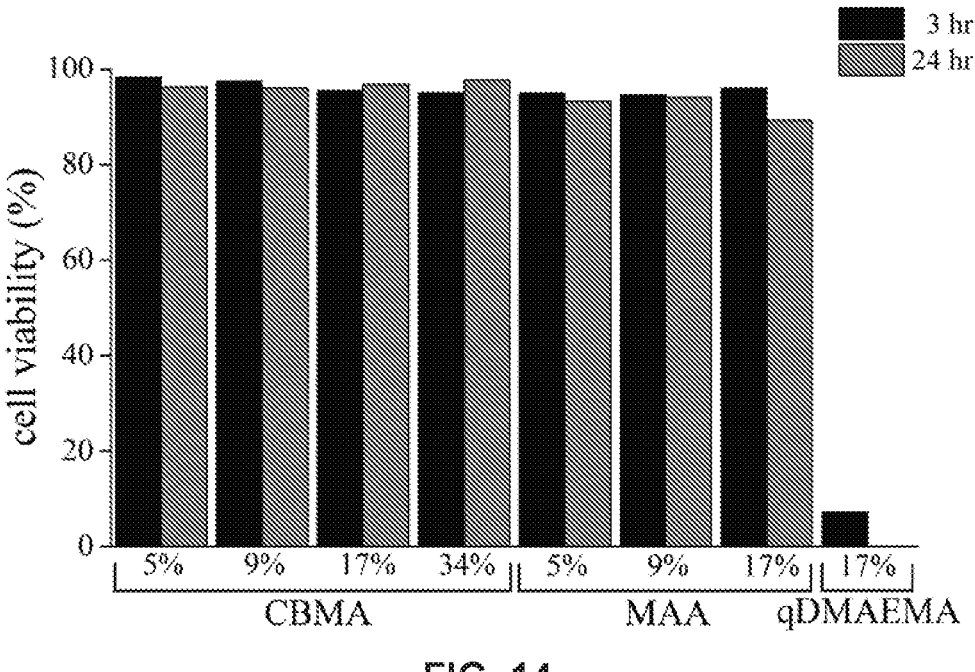
FIG. 14 is a bar graph showing cell viability (%) in anionic (MAA), zwitterionic (CBMA), and cationic (qD-MAEMA) microgels.

FIG. 14 is a bar graph showing cell viability (%) in anionic (MAA), zwitterionic (CBMA), and cationic (qDMAEMA) microgels.

Figure 15:
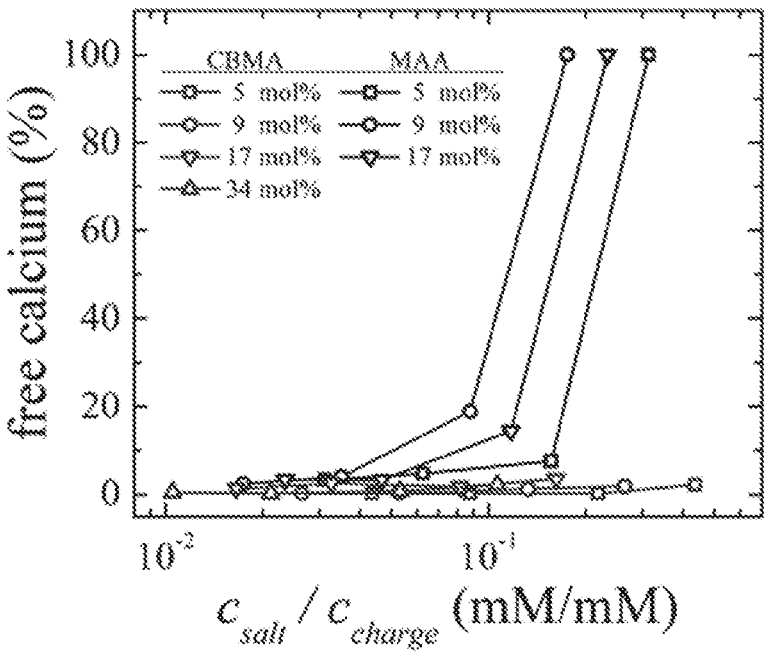
FIG. 15 is a graph showing fee calcium (%) as a function of $c_{salt}/c_{charge}$ (mM/mM) for anionic (MAA) and zwitterionic (CBMA) microgels.

FIG. 15 is a graph showing fee calcium (%) as a function of $c_{salt}/c_{charge}$ (mM/mM) for anionic (MAA) and zwitterionic (CBMA) microgels.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A three-dimensional cell growth medium, the three-dimensional cell growth medium consisting of:
   a plurality of microgel particles, wherein each of the plurality of microgel particles consists of a crosslinked polymeric network, and wherein the crosslinked polymeric network consists of:
      low charge density polymer molecules, wherein each of the low charge density polymer molecules consists of a first set of neutral monomer units derived from acrylamide and a second set of charged monomer units derived from methacrylic acid, wherein an average spacing between the charged monomer units is greater than the Bjerrum length; and
      a crosslinker;
      wherein a molar ratio of the first monomer to the crosslinker present in the solution is between 20:1 and 200:1; and
   a liquid cell culture medium, wherein the plurality of microgel particles swell with the liquid cell culture medium to form a three-dimensional granular gel; and
   wherein the three-dimensional cell growth medium is a yield stress material.

2. The three-dimensional cell growth medium of claim 1, wherein the charged groups are negatively charged groups.

3. The three-dimensional cell growth medium of claim 1, wherein less than 60% of the sum of the first and second sets of monomer units are second monomer units.

4. The three-dimensional cell growth medium of claim 1, wherein less than 20% of the sum of the first and second sets of monomer units are second monomer units.

5. The three-dimensional cell growth medium of claim 1, wherein the crosslinker has an average molecular weight of between 250 g/mol and 10,000 g/mol.

6. The three-dimensional cell growth medium of claim 1, wherein the crosslinker is selected from poly(ethylene glycol) diacrylate (PEGDA) or N,N'-methylenebisacrylamide (MBA).

7. The three-dimensional cell growth medium of claim 1, wherein the crosslinker is hydrophilic.

* * * * *